(12) United States Patent
Hammond et al.

(10) Patent No.: US 8,114,915 B2
(45) Date of Patent: Feb. 14, 2012

(54) METHOD AND SYSTEM FOR HANDLING SLURRIES OF VARYING LIQUID RATES AND SOLIDS CONTENT

(75) Inventors: David G. Hammond, Fairfax, VA (US); Jorge L. Soto, Centreville, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 92 days.

(21) Appl. No.: 12/590,581

(22) Filed: Nov. 10, 2009

(65) Prior Publication Data

US 2010/0144906 A1 Jun. 10, 2010

Related U.S. Application Data

(60) Provisional application No. 61/201,067, filed on Dec. 5, 2008.

(51) Int. Cl.
*C07C 27/00* (2006.01)
*B01D 21/26* (2006.01)

(52) U.S. Cl. .......................... 518/700; 210/787; 210/800

(58) Field of Classification Search .................. 518/700; 210/787, 800
See application file for complete search history.

(56) References Cited

U.S. PATENT DOCUMENTS

| | | |
|---|---|---|
| 3,505,204 A | 4/1970 | Hoffman |
| 3,607,113 A | 9/1971 | Featherston |
| 4,230,556 A | 10/1980 | Carr et al. |
| 5,157,054 A | 10/1992 | Herbolzheimer et al. |
| 5,356,845 A * | 10/1994 | Clavenna et al. ............... 502/21 |
| 5,776,988 A | 7/1998 | Chaumette et al. |
| 5,866,621 A | 2/1999 | Behrmann et al. |
| 5,900,159 A | 5/1999 | Engel et al. |
| 6,096,789 A | 8/2000 | Clerici et al. |
| 6,331,196 B1 | 12/2001 | Alperovitch |
| 6,420,497 B1 | 7/2002 | Kufeld et al. |
| 6,462,098 B1 | 10/2002 | Vogel et al. |
| 6,716,887 B2 | 4/2004 | Newton et al. |
| 6,730,221 B2 | 5/2004 | Bohn et al. |
| 6,833,078 B2 | 12/2004 | Espinoza et al. |
| 6,903,141 B2 | 6/2005 | Zhou et al. |
| 7,078,439 B2 | 7/2006 | Odueyungbo et al. |
| 7,111,738 B2 | 9/2006 | Allen, III |
| 2004/0050806 A1* | 3/2004 | Espinoza et al. ............... 210/806 |
| 2004/0171702 A1* | 9/2004 | Odueyungbo et al. ........ 518/715 |
| 2004/0250973 A1 | 12/2004 | Johns et al. |
| 2005/0004238 A1 | 1/2005 | Clerici et al. |

OTHER PUBLICATIONS

J. K. Neathery, et al., Quarterly Report, "Separation of Fischer-Tropsch Wax Products from Ultrafine Iron Catalyst Particles", Reporting period—Apr. 1, 2005 to Sep. 30, 2005, The University of Kentucky Center for Applied Energy Research, DE-FC26-03NT41965.

* cited by examiner

*Primary Examiner* — Jafar Parsa

(57) ABSTRACT

A method and system for collecting a plurality of slurries containing solid particles of varying particle size distribution and amount and performing a classification and separation on the slurries is provided whereby a fines-rich stream and a stream containing substantially coarse particles is obtained. The method and system includes separating the fines from the slurry liquid and thickening the separated coarse particles in a settling zone for subsequent use.

7 Claims, 2 Drawing Sheets

METHOD AND SYSTEM FOR HANDLING SLURRIES OF VARYING LIQUID RATES AND SOLIDS CONTENT

Non-Provisional Application based on Provisional Application No. 61/201,067 filed Dec. 5, 2008.

FIELD OF THE INVENTION

The present invention relates to a method and system for handling slurries that are generated in varying rates and volumes and contain varying solids content. In particular, the present invention relates to a method and system for classifying suspended matter and the suspending liquid in such slurries.

BACKGROUND OF THE INVENTION

There are numerous industrial processes in which fluid streams are generated containing suspended solids which ultimately require separation and classification of the solids from the suspending liquid. An example of such an industrial process is the Fischer-Tropsch three-phase slurry process for the synthesis of hydrocarbons.

Typically, a Fischer-Tropsch three-phase slurry, hydrocarbon synthesis process is conducted in a bubble column reactor by contacting a stream of synthesis gas (comprising $H_2$ and CO) with a liquid suspension of solid catalyst. The synthesis gas will have an $H_2$:CO molar ratio of from about 1:1 to about 3:1. The dispersing liquid is primarily linear hydrocarbon reaction product. To facilitate contact between catalyst and the synthesis gas, the gas is fed into the bottom of the bubble column through a gas distributor that produces small gas bubbles. As the synthesis gas bubbles rise through the column, they not only disperse the catalyst in the liquid, but they also react to form hydrocarbon products that are mainly liquids under the reaction temperature and pressure conditions. Any gaseous products that are formed rise to the top of the reactor from which they are removed.

Because it is necessary to maintain the slurry in the reactor at a constant level, liquid products are continuously or periodically removed from the reactor. In doing so, however, it is important to separate dispersed catalyst particles from the liquid being removed to maintain a constant inventory of catalyst in the reactor. Generally, the separation is conducted in a filtration zone located in the slurry bed. The filtration zone typically comprises cylindrical filtering media through which liquid passes from the exterior to the interior of the filtering media where it is collected and removed from the reactor. In some reactor designs, liquid product is filtered in an external filtration system, and separated catalyst is returned to the reactor.

Over time, the hydrodynamic conditions existing in the bubble column result in some attrition of the catalyst, thereby forming catalyst particles known as "fines". Fines are those particles having a size less than 10 microns. In contrast, coarse catalyst particles are those particles having a size greater than or equal to 10 microns. The size of the openings in the filtering media will, of course, determine the amount of fines likely to pass through the filter with the liquid product. Thus, the liquid product removed from the bubble column may be subjected to a second stage separation process to provide a substantially fine-free liquid product and a second stage solids-containing stream requiring further liquids-solids separation. The volume and solids content of the second stage stream will vary depending upon the extent of catalyst attrition. Also, over time, fines not passing through the filter will begin to plug the filter. Consequently, filter efficiency is decreased, and remedial action such as backwashing with a liquid stream becomes necessary. Backwashing the filters typically is conducted periodically in a pulsing mode with a liquid. This results in an undesirable accumulation of fines in the slurry. Consequently, it is necessary to control the amount of fines that accumulates in the slurry. Thus, a slip stream containing fines may be removed when necessary, and this fines-laden slip stream may be subjected to separation and classification.

As is known in the art, the catalyst used in a three-phase slurry reactor is regenerated either continuously or periodically. Typically, the catalyst is regenerated when its activity decreases to the point where reactant conversion cannot be maintained. In the regeneration process, the first step generally requires the removal of wax from the catalyst. In one method, this is accomplished by washing the catalyst with a solvent. The solvent typically is separated from the catalyst by decanting, thereby providing a liquid stream containing solids, primarily fines. These solids also require classification and separation from the liquid.

Obviously, the rate of flow of catalyst-containing stream used to control the slurry fines concentration will be different from that generated in the regeneration step as will their solids content and particle size distribution. So too will it be different from the solids-containing stream generated in the above mentioned second stage separation process.

Other sources of solids-containing liquid streams requiring solids classification and separation are those obtained from occasional flushing of the bubble column reactor cone, unit purges, process equipment flushes, etc. These, of course, will be generated at different times, at varying rates, and will have different solids content.

An object of this present invention is to provide a method and system for classifying and separating solids suspended in liquid streams that are generated at varying rates and which contain differing amounts of solids.

Another object of the invention is to provide an integrated system for particle size classification and for solids thickening, which system is capable of functioning under differing load conditions.

These and other objects of the invention will become apparent from the description of the invention below.

SUMMARY OF THE INVENTION

Broadly stated, the invention features a method and system for collecting a plurality of slurries from one or more sources that contain solid particles of varying particle size distribution and amount. A classification separation is performed on the collected slurries to provide a fines-rich stream and a stream containing substantially coarse solid particles.

In particular embodiments, one or more of the following features may be included. The slurry collected may be held in the collection system for a selected period of time and the solids maintained in suspension by mechanical agitation. The coarse fraction may be collected and thickened in a settling zone before subsequent treatment or use. The fines-rich stream may be sent to a solids concentration unit for separation of the fines from the slurry liquid.

The method and system of the present invention is particularly useful in collecting various slurry streams, other than the primary product stream, from a three-phase slurry process. The collected streams are then subjected to a classification separation.

Specific embodiments and other features of the method and system of the invention will be described in the detailed description of the invention below.

DETAILED DESCRIPTION OF THE INVENTION

Figure 1:
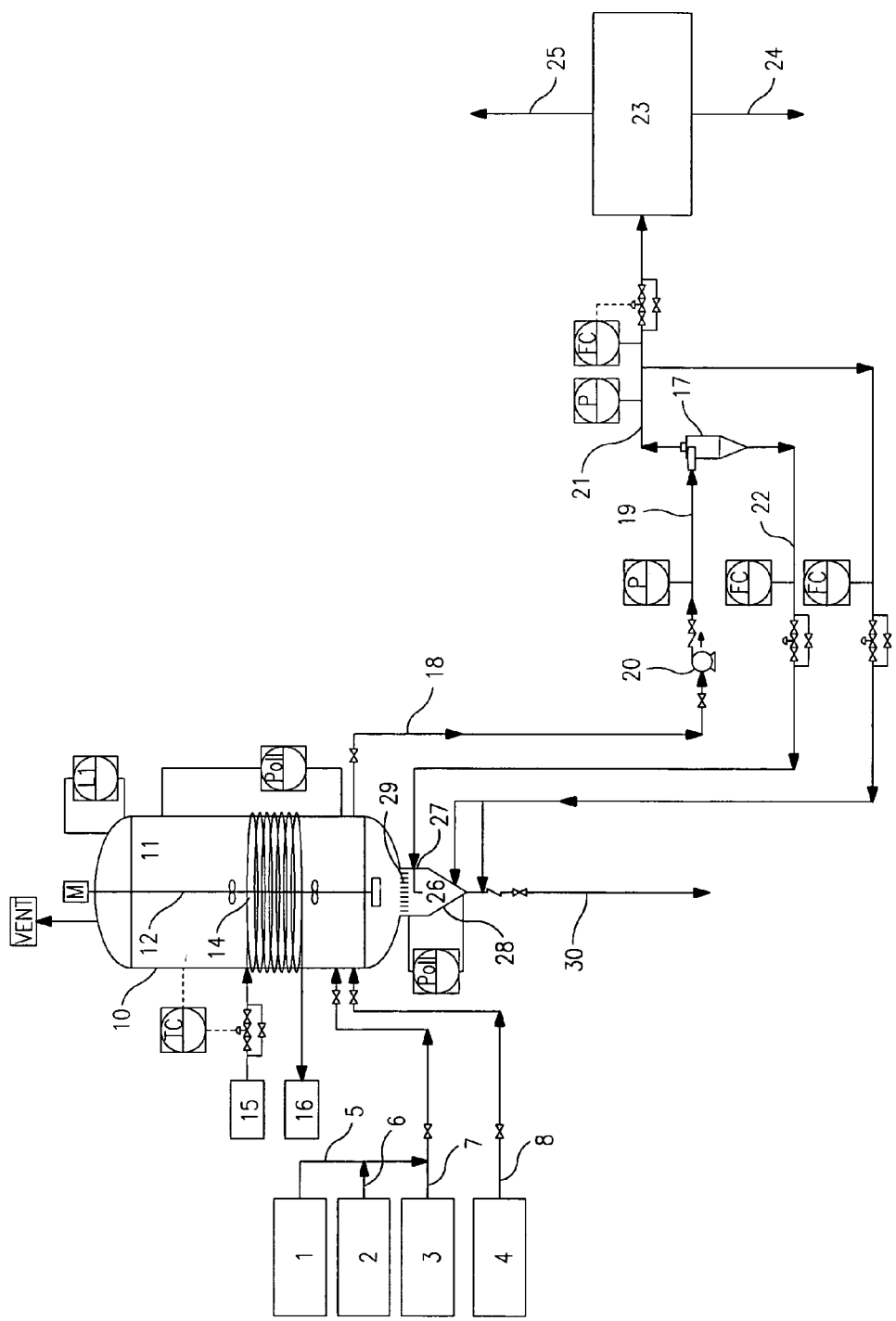
FIG. 1 is a schematic diagram depicting one embodiment of the present invention.

The present invention is applicable to industrial processes which generate slurry streams that require the separation and classification of the solid matter in those streams. Indeed, the invention is particularly applicable to three-phase slurry processes. A specific example of such a process is the Fischer-Tropsch synthesis process. For convenience, the invention will be described by specific references to the Fischer-Tropsch hydrocarbon synthesis process.

Suitably, the reactor for the Fischer-Tropsch synthesis process is a bubble column reactor comprising a vertical vessel for containing a catalyst suspended in a liquid phase through which synthesis gas is bubbled.

Also suitably, the reactor will include one or more gas disengaging vertical downcomers which assist in the circulation of slurry in the reactor.

As indicated previously, the synthesis gas comprises $H_2$ and CO in the molar ratio of 1:1 to 3:1.

The slurry liquid comprises those linear hydrocarbon reaction products that are liquids at reaction conditions.

Suitable Fischer-Tropsch hydrocarbon synthesis catalysts include effective amounts of Co and one or more of Re, Ru, Fe, Ni, Th, Zr, Hf, Mg and La on a suitable inorganic support.

The Fischer-Tropsch reaction is carried out at temperatures, pressures and hourly gas space velocities in the range of about 320° F. to 850° F., 80 to 600 psi and 100 to 40,000 V/hr/V, expressed as standard volumes of the syngas mixture (60° F., 1 atm) per hour per volume of catalyst, respectively.

In the operation of the Fischer-Tropsch process liquid products will be removed from the reactor through internal filters to provide a primary product stream. Optionally, the slurry liquids may be sent to a filter system located outside the reactor for the separation of liquid products from catalyst solids to provide the primary product stream.

Also during the operation of the Fischer-Tropsch process, a slurry slip stream will be processed to generate a fines-laden secondary stream, either in a continuous or batch mode, to control the slurry fines content. This secondary liquid stream that will require separation and classification of the solids.

Other sources of solids-containing secondary streams that may be generated include the liquid collected from flushing the reactor cone, the decant liquid obtained from washing catalyst before regeneration, reactor purges, and equipment processing flushes.

In the present invention any one or all of these secondary streams may be treated in the system of the invention. Thus in one aspect of the invention, a Fischer-Tropsch hydrocarbon synthesis plant is provided which includes the solids classification and separation system described herein.

A first embodiment of the system of this invention and its integration into a Fischer-Tropsch hydrocarbon synthesis process will now be described by reference to FIG. 1. As shown, various sources 1, 2, 3 and 4 of slurry liquids from a Fischer-Tropsch process are provided with conduits 5, 6, 7 and 8 for transfer of their respective slurries for collection in upper section 11 of collection drum 10. The upper section 11 of collection drum 10 includes mechanical mixing means 12 for keeping the solids suspended in the slurries collected in drum 10. Heating means also is provided in drum 10 to prevent the cooling and solidification of wax product in the slurry. One such heating means is a coiled conduit 14 through which steam from a steam source 15 is circulated. This heating means also includes means 16 for receipt of condensate. Other heating means may include hot oil, electric heating jackets and the like.

The slurry collected in drum 10 is classified and separated when appropriate by withdrawing slurry from drum 10 and transferring it to a hydrocyclone 17.

Hydrocyclones are devices in which a liquid feed is subjected to centrifugal forces by a rotating movement of the feed caused by a tangentially directed inlet. During the rotating movement, liquid with coarse catalyst particles concentrate at the bottom of the hydrocyclone while liquid with catalyst fines concentrate at the head of the hydrocyclone.

As shown in FIG. 1, slurry liquid is withdrawn via conduit 18 from the side of drum 10 and pumped by pumped by pump 20 via conduit 19 into hydrocyclone 17. Although a centrifugal pump 20 is shown schematically in the Figure, it is preferred that the pump used be a positive displacement pump and especially a progressive cavity pump to minimize attrition of the catalyst.

As shown in FIG. 1, hydrocyclone 17 has a top conduit 21 for removal of an overflow stream and a bottom conduit 22 for removal of an underflow stream. The overflow stream may be transferred to a solids concentration unit 23, such as a cross-flow type separation device, in which the fines are collected and removed via line 24 for disposal or reclaiming and liquid product is removed via line 25 for further processing.

The underflow stream removed via line 22 from hydrocyclone 17 is transferred to a settling zone shown as the bottom section 26 of drum 10. Bottom section 26 is encompassed by a cylindrical part 27 and a bottom cone-shaped part 28. Also, bottom section 26 is separated from the top section 11 of drum 10 by a plurality of stilling baffles 29.

The bottom section 26 operates much like a thickener with coarse catalyst solids settling in the cone 28. In a traditional thickener, clarified liquid is separated from solids using an overflow weir or draw-off nozzle. In this embodiment of the present invention, liquid is fed into section 26 and then rises into the upper section 11 of drum 10. Preferably, the liquid used is a portion of the overflow stream of hydrocyclone 17.

The coarse catalyst collected in section 26 of drum 10 is removed via line 30 and may be sent, for example, to a catalyst regeneration unit dewaxing drum (not shown) for dewaxing and then regeneration.

In the first embodiment just described, only one hydrocyclone is shown; however, optionally a bank of hydrocyclones may be used.

Also, in the first embodiment just described, only one collection drum is used; however, optionally a second collection drum may be employed and operably connected to sources 1, 2, 3 and 4 and having the elements described in connection with the FIG. 1 single drum embodiment.

Whether one or two drums are used in the practice of the invention, it is preferred that they have a sufficient capacity to allow for variability in slurry flow rate based on the design capacity and output of the Fischer-Tropsch process with which they are integrated. For example, each drum preferably is sized to have a one day hold up capacity. In this way, the classification and separation system of the invention may be operated independently of the operation of the hydrocarbon synthesis process. It also allows for short maintenance periods on downstream equipment without impacting the ability to receive slurry feeds from the synthesis process.

Figure 2:
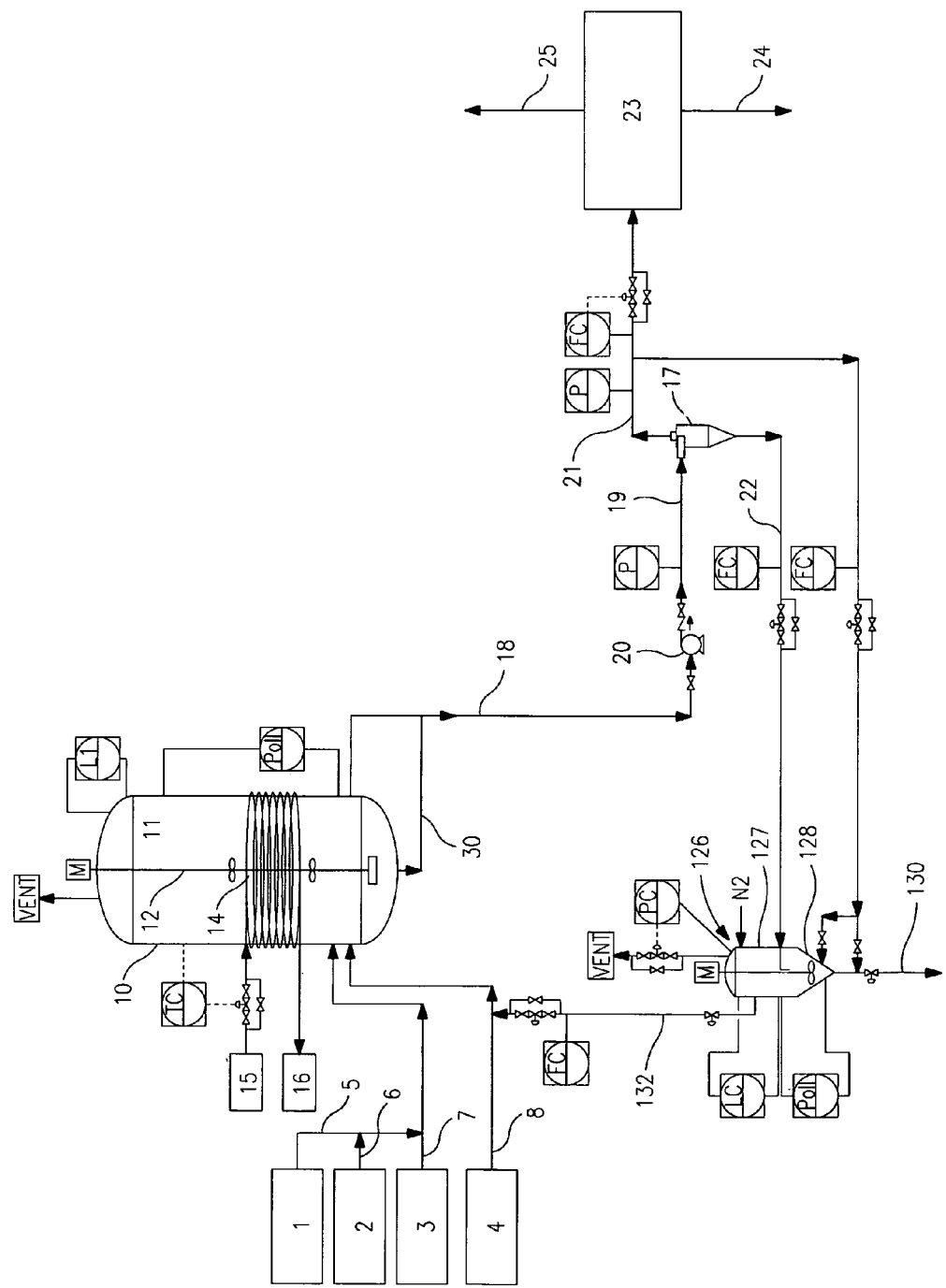
FIG. 2 is a schematic diagram illustrating another embodiment of the invention. These embodiments are described in detail below.

Another and preferred embodiment of the invention is depicted schematically in FIG. 2. In this embodiment, instead of a coarse catalyst settling zone being integral with the collector drum 10, a separate external settling zone, i.e., vessel 126, is used as a coarse catalyst collection section. As shown in FIG. 2, vessel 126 has a cylindrical part 127 and a bottom cone-shaped part 128. Optionally, vessel 126 may also be provided with a mixing device 129. In operation, slurry liquid is withdrawn from collection drum 10 via conduit 18 and is sent to hydrocyclone 17. The underflow stream 22 from hydrocyclone 17 is sent via conduit 22 to the coarse catalyst collection vessel 126. Liquid separated from the solids in vessel 126 is sent to drum 10 via line 132, while collected solids may be removed via line 130. In this embodiment, vessel 126 preferably is operated at elevated pressure, thereby eliminating the need to provide pumps to transfer the separated liquid to drum 10. As with the FIG. 1 embodiment, optionally a second collection drum may be provided, if desired, and operated substantially similarly to the single drum embodiment.

What is claimed is:

1. In a three-phase slurry process wherein a plurality of liquid slurries are generated having different volumes and different solids content all of which require solids classification and separation, the improvement comprising:
   collecting the slurries as generated in one or more collection drums;
   agitating the collected slurries to maintain the solids therein suspended;
   withdrawing the collected slurries from the drum or drums when separation and classification is desired; and
   transferring the withdrawn slurries to a hydrocyclone wherein an overflow stream enriched in fines is obtained and an underflow stream containing coarse particles is obtained whereby the solids in said slurries is classified and separated.

2. The improvement of claim 1 wherein the overflow stream is transferred to a solids concentration zone where solids are separated from the liquid in the overflow zone.

3. The improvement of claim 1 wherein the underflow stream is transferred to a settling zone for thickening.

4. The improvement of claim 3 wherein the settling zone comprises a bottom section of the collection drum or drums.

5. The improvement of claim 3 wherein the settling zone comprises a vessel is separate from the collection drum or drums.

6. A Fischer-Tropsch hydrocarbon synthesis process comprising:
   contacting synthesis gas with a hydrocarbon synthesis catalyst in a three-phase slurry bubble column under Fischer-Tropsch hydrocarbon synthesis conditions;
   processing a portion of the reactor slurry within or outside of the bubble column to provide a fines-laden slurry stream;
   removing catalyst of reduced activity from the bubble column for regeneration and subsequent return to the bubble column wherein the removed catalyst is first washed with liquid prior to regeneration thereby providing a slurry stream;
   collecting at least the fines-laden slurry stream and the slurry stream from pre-regeneration washing in a collection drum or drums;
   agitating and heating the collected slurries to maintain the solids therein in suspension and to prevent wax therein to solidify;
   transferring at a selected time the collected slurries to a hydrocyclone or bank of hydrocyclones to provide a fines-containing overflow stream or streams and a coarse catalyst-containing underflow stream or streams;
   transferring the overflow stream(s) to a solids concentration zone;
   removing solids from the concentration zone;
   removing liquid from the concentration zone and transferring for upgrading;
   transferring the underflow stream(s) to a solids settling zone; and
   periodically removing the solids from the settling zone and transferring it to the catalyst regeneration system.

7. The improvement of claim 1, wherein the collected slurries comprise: internally or externally filtered process liquid products removed as slurries from the reactor; a fines-laden secondary stream processed from a slurry slip stream from the reactor; and optionally one or more streams selected from the group consisting of liquid collected from flushing a reactor cone, decant liquid from washing catalyst before regeneration, slurry/liquid from reactor purges, and slurry/liquid from equipment processing flushes.

* * * * *